United States Patent
Van Der Puy et al.

(10) Patent No.: US 7,786,333 B2
(45) Date of Patent: Aug. 31, 2010

(54) PROCESS FOR THE MANUFACTURE OF FLUORINATED OLEFINS

(75) Inventors: Michael Van Der Puy, Amherst, NY (US); George R. Cook, Buffalo, NY (US); Peter H. Sheidle, Wheatfield, NY (US); Kevin D. Uhrich, Alden, NY (US); Haiyou Wang, Amherst, NY (US); Hsueh Sung Tung, Getzville, NY (US)

(73) Assignee: Honeywell International, Inc., Morristown, NJ (US)

( * ) Notice: Subject to any disclaimer, the term of this patent is extended or adjusted under 35 U.S.C. 154(b) by 0 days.

(21) Appl. No.: 12/389,110

(22) Filed: Feb. 19, 2009

(65) Prior Publication Data

US 2009/0209791 A1    Aug. 20, 2009

Related U.S. Application Data

(62) Division of application No. 11/588,464, filed on Oct. 27, 2006, now Pat. No. 7,560,602.

(60) Provisional application No. 60/763,086, filed on Jan. 27, 2006, provisional application No. 60/733,355, filed on Nov. 3, 2005.

(51) Int. Cl.
*C07C 17/00* (2006.01)
*C07C 17/10* (2006.01)

(52) U.S. Cl. ............... 570/156; 570/157; 570/175; 570/176

(58) Field of Classification Search .......... 570/156, 570/157, 175, 176
See application file for complete search history.

(56) References Cited

U.S. PATENT DOCUMENTS

| | | | |
|---|---|---|---|
| 4,033,899 A | 7/1977 | Bennett et al. | |
| 4,138,355 A | 2/1979 | Ferstandig | |
| 5,180,860 A | 1/1993 | Fernandez et al. | |
| 5,334,783 A | 8/1994 | Freudenreich et al. | |
| 5,396,000 A * | 3/1995 | Nappa et al. | 570/175 |
| 5,672,787 A | 9/1997 | Bielefeldt et al. | |
| 5,679,875 A | 10/1997 | Aoyama et al. | |
| 5,710,352 A | 1/1998 | Tung | |
| 5,895,639 A | 4/1999 | Swain et al. | |
| 5,945,573 A | 8/1999 | Nappa et al. | |
| 5,986,151 A | 11/1999 | Van Der Puy | |
| 6,031,141 A | 2/2000 | Mallikarjuna et al. | |
| 6,093,859 A | 7/2000 | Nappa et al. | |
| 6,194,619 B1 | 2/2001 | Rao et al. | |
| 6,229,058 B1 | 5/2001 | Sievert et al. | |
| 6,369,284 B1 | 4/2002 | Nappa et al. | |
| 6,395,700 B1 | 5/2002 | Yamada et al. | |
| 6,548,719 B1 | 4/2003 | Nair et al. | |
| 7,189,884 B2 | 3/2007 | Mukhopadhyay et al. | |
| 7,230,146 B2 | 6/2007 | Merkel et al. | |
| 7,285,690 B2 | 10/2007 | Rao et al. | |
| 7,285,692 B2 | 10/2007 | Rao et al. | |
| 7,371,363 B2 * | 5/2008 | Merkel et al. | 423/488 |
| 2004/0236161 A1 | 11/2004 | Rao et al. | |
| 2005/0090698 A1 | 4/2005 | Merkel et al. | |
| 2005/0245773 A1 | 11/2005 | Mukhopadhyay et al. | |
| 2005/0245774 A1 | 11/2005 | Mukhopadhyay et al. | |
| 2006/0106263 A1 | 5/2006 | Miller et al. | |

FOREIGN PATENT DOCUMENTS

WO    9833755    8/1998

OTHER PUBLICATIONS

Knunyants I. .L, et al.: "Reactions of Fluoro Olefins Communication 13, Catalytic Hydrogenation of Perfluoro Olefins", Bulletin of the Academy of Sciences of the USSR, Division of Chemical Sciences, 1960, XP000578879, pp. 1312-1317.

* cited by examiner

*Primary Examiner*—Jafar Parsa
(74) *Attorney, Agent, or Firm*—Bruce O. Bradford

(57) ABSTRACT

A process for the production of fluorinated olefins, preferably fluorinated propenes, by contacting a feed stream containing a fluorinated olefin and hydrogen with a first amount of catalyst to produce the hydrofluorocarbon, wherein a first exit stream contains unreacted fluorinated olefin and hydrogen; contacting the first exit stream with a second amount of catalyst to produce a hydrofluorocarbon, wherein the second amount of catalyst is preferably greater than the first amount of catalyst; and contacting the hydrofluorocarbon with a catalyst for dehydrohalogenation to produce a product stream of fluorinated olefin.

18 Claims, 1 Drawing Sheet

PROCESS FOR THE MANUFACTURE OF FLUORINATED OLEFINS

CROSS-REFERENCES TO RELATED APPLICATIONS

This application is a divisional of U.S. application Ser. No. 11/588,464 filed on Oct. 27, 2006 (now U.S. Pat. No. 7,560,602), which is related to and claims the priority benefit of provisional U.S. Application 60/733,355, filed on Nov. 3, 2005, both of which are incorporated herein by reference.

This application is also related to provisional U.S. Application 60/763,086 filed on Jan. 27, 2006, which is incorporated herein by reference.

Also incorporated herein by reference are U.S. application Ser. No. 11/588,465 filed on Oct. 27, 2006 and U.S. application Ser. No. 11/588,671 filed on Oct. 27, 2006.

BACKGROUND OF THE INVENTION

Fluorinated olefins, as a class, have many and varied uses, including as chemical intermediates and monomers.

Several methods for preparing fluorinated olefins are known. For example, U.S. Pat. No. 5,679,875 discloses methods for manufacturing 1,1,1,2,3-pentafluoropropene and 1,1,1,2,3-pentafluoropropane; U.S. Pat. No. 6,031,141 discloses a catalytic process using chromium-containing catalysts for the dehydrofluorination of hydrofluorocarbons to fluoroolefins; U.S. Pat. No. 5,396,000 discloses a process for producing $CF_3CHFCH_2F$ using vapor phase catalytic dehydrohalogenation to produce $CF_3CF=CHF$ and HF, followed by vapor phase catalytic hydrogenation of $CF_3CF=CHF$ in the presence of HF; U.S. Pat. No. 6,548,719 discloses a process for producing fluoroolefins by dehydrohalogenating a hydrofluorocarbon in the presence of a phase transfer catalyst; U.S. Publication No. 2006/0106263 discloses the production and purification of hydrofluoroolefin compounds; and WO98/33755 discloses catalytic process for the dehydrofluorination of hexafluoropropanes to pentafluoropropenes.

Applicants have discovered that the processes of the type described above have disadvantages and/or are not as effective and/or economical as would be practically necessary for large scale commercial production. For example, applicants have come to appreciate that it is generally not possible, by following the teachings of the above publications alone, to achieve a process having at once a high degree of ultimate conversion and a high degree of selectivity to the desired fluorinated olefin.

SUMMARY OF THE INVENTION

Applicants have come to appreciate in one respect of the invention, that none of the above-noted publications disclose an integrated process comprising the steps of selectively hydrogenating one or more highly fluorinated olefins to produce one or more hydrofluorocarbons, followed by the step of dehydrofluorinating the resultant hydrofluorocarbons(s) to produce one or more desired fluorinated olefins, particularly propene, and HF, nor do they disclose such a process combined with a highly effective HF recovery step.

Applicants have developed, in one aspect of the present invention, processes for the synthesis of fluorinated alkenes, and preferable fluorinated olefins having from three to six carbon atoms and a degree of fluorine substitution of N. In certain highly preferred embodiments, the desired fluorinated olefins of the present invention comprise one or more C2 to C6 fluoroalkenes, preferably compounds having a formula as follows:

$$X^1CFzR3-z$$

where $X^1$ is a C1, C2, C3, C4, or C5 unsaturated, substituted or unsubstituted, alkyl radical, each R is independently Cl, F, Br, I or H, and z is 1 to 3. Highly preferred among such compounds are propenes and butenes having from 3 to 5 fluorine substituents, and among these tetrafluoropropenes (HFO-1234) are especially preferred.

Preferred processes of the present invention comprise reacting a fluorinated olefin starting material with a degree of halogen substitution of N+1 having substantially the same number of carbon atoms as the fluorinated olefin(s) to be synthesized with a degree of halogen substitution of N. Preferably the fluorinated olefin starting material having a degree of fluorine substitution of N+1 is exposed to reaction conditions effective to produce a reaction product containing one or more fluorinated alkanes having the same number of carbons atoms as the olefin. In one preferred aspect of the present invention, this olefin conversion step comprises a reaction that is sometimes referred to herein for convenience, but not necessarily by way of limitation, as a reduction or hydrogenation step. The fluorinated alkane is then preferably converted to a fluorinated olefin having a degree of fluorine substitution of N. In one preferred aspect of the present invention, this alkane conversion step comprises a reaction that is sometimes referred to herein for convenience, but not necessarily by way of limitation, as a dehydrohalogenation reaction or more particularly in certain embodiments as a dehydrofluorination or dehydrochlorination reaction.

According to one aspect of the present invention, the present processes preferably comprise the steps of
(a) hydrogenating, preferably in a multistage reaction, a compound of formula (I)

$$(CX_nY_{3-n})(CR^1{}_aR^2{}_b)_zCX=CH_mX_{2-m} \quad (I)$$

under conditions effective to form at least one fluorinated alkane of formula (II)

$$(CX_nY_{3-n})(CR^1{}_aR^2{}_b)_zCHXCH_{m+1}X_{2-m} \quad (II)$$

where:
each X is independently Cl, F, I or Br;
each Y is independently H, Cl, F, I or Br;
each $R^1$ is independently H, Cl, F, I, Br or unsubstituted or halogen substituted methyl or ethyl radical;
each $R^2$ is independently H, Cl, F, I, Br or unsubstituted or halogen substituted methyl or ethyl radical;
n is 1, 2 or 3;
a and b are each 1 or 2, provided that a+b=2;
m is 0, 1 or 2; and
Z is 0, 1, 2 or 3, and
(b) deydrohalogenating the compound of formula (II) under conditions effective to produce a fluoroolefin with a lower degree of fluorine substitution than the compound of formula (I), preferably to produce a compound of formula (III):

$$(CX_nY_{3-n})(CR^1{}_aR^2{}_b)_zCX=CH_mX_{2-m} \quad (III)$$

where each n is the same value as in formula (I) and m is 0 or 1.

In certain preferred embodiments, the reactant of formula (I) comprises a three carbon olefin of formula (IA) wherein z is 0, namely $$CX_nY_{3-n}CX=CH_mX_{2-m} \quad (IA)$$

to produce a three carbon alkane of formula (IIA) as follows:

$$(CX_nY_{3-n})CHXCH_{m+1}X_{2-m} \quad (IIA)$$

where X, Y, n, and m are all as indicated above, which compound is then dehydrohalogenated to form a compound of formula (IIIA)

$$(CX_nY_{3-n})CX=CH_mX_{2-m} \quad (IIIA)$$

where n is the same value as in formula (IA) and m is 0 or 1.

In certain highly preferred aspects of such embodiments, a saturated terminal carbon of the compounds of formulas (I) or (IA) is fully substituted with fluorine (for example, n on the saturated terminal carbon is 3 and each X on that carbon is F), and even more preferably n is 3 and each X in the compound is F.

For three carbon embodiments of such preferred aspects, the compound of Formula (IA) is preferably a fluoropropene having from three to six fluorine substituents, and potentially other halogen substituents, including for example hexafluoropropene (that is, Z is 0, n is 3, m is 0, and all X are F) or pentafluoropropene (that is, Z is 0, n=3, m is 1, and all X are F), and the compound of formula (IIA) preferably comprises, and more preferably is selected from the group consisting of, one or more of the following fluorinated alkanes: chlorotrifluoropropane (HCFC-244) and pentafluoropropane (HFC-245), and hexafluoropropane (HFC-236), including all isomers of each of these, but preferably 1-chloro, 1,3,3,3-tetrafluoropropane (HCFC-244fa), 1,1,1,3,3-pentafluoropropane (HFC-245fa), 1,1,1,2,3-pentafluoropropane (HFC-245eb), and 1,1,1,2,3,3-hexafluoropropane (HFC-236ea). In certain preferred embodiments the fluorinated alkane produced by the conversion step has a degree of fluorine substitution of N+1.

In preferred embodiments, the converting step (a) wherein the olefin is converted to an alkane is carried out under conditions effective to provide a formula (I) conversion of at least about 40%, more preferably at least about 55%, and even more preferably at least about 70%. In certain preferred embodiments the conversion is at least about 90%, and more preferably about 99%. Further in certain preferred embodiments, the conversion of the compound of formula (I) to produce a compound of formula (II) is conducted under conditions effective to provide a formula (II) selectivity of at least about 60%, more preferably at least about 80%, and more preferably at least about 90%, and even more preferably about 100%.

In preferred embodiments, the converting step (b) wherein the alkane is converted to a fluorinated olefin having a degree of fluorination of N is carried out under conditions effective to provide a formula (II) conversion of at least about 40%, more preferably at least about 55%, and even more preferably at least about 70%. In certain preferred embodiments the conversion is at least about 90%, and more preferably about 95%. Further in certain preferred embodiments, the conversion of the compound of formula (II) to produce a compound of formula (III) is conducted under conditions effective to provide a formula (III) selectivity of at least about 60%, more preferably at least about 80%, and more preferably at least about 90%, and even more preferably about 98%.

DETAILED DESCRIPTION

Figure 1:
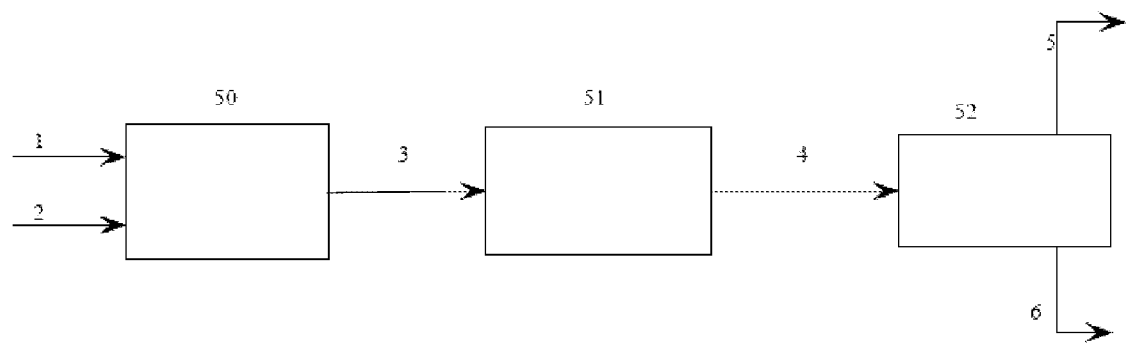
FIG. 1 is a schematic process flow diagram according to one embodiment of the present invention.

One embodiment of the present invention will now be described in connection with FIG. 1 in which a feed stream 1 comprising at least one fluorinated olefin having a degree of halogen substitution, and preferably a degree of fluorine substitution, of N+1 is subjected to a first converting step 50. The converting step 50 preferably involves also a feed stream 2 comprising a reducing agent. The converting step 50 preferably includes providing one or more reaction vessels, at least one of which preferably contains a reduction or hydrogenation catalyst, and introducing streams 1 and 2 into the vessel(s) under conditions effective to achieve the desired conversion.

Although the streams 1 and 2 in the figure are shown for convenience as being separate streams, this is done for convenience and the present invention is not so limited. For example, the streams could in certain embodiments be combined outside the vessel and then introduced to the vessel together, or in other embodiments stream 1 and stream 2 might each comprise several separate streams, each of which is introduced into the vessel(s) at different times and/or at different locations. This same convention has been used and applies herein throughout to all use of the term "stream," both in the description and in the figures, unless specifically indicated otherwise.

The preferred converting step 50 produces at least one reaction product stream 3 which contains a fluorinated alkane in accordance with the present invention. Stream 3 is used as a reactant in conversion step 51, optionally stream 3 is further purified before fed to step 51, wherein the fluorinated alkane in stream 3 is converted to a fluorinated olefin have a degree of halogen substitution, and in certain preferred embodiments fluorine substitution, of N in accordance with the present invention. The converting step 51 preferably includes providing one or more reaction vessels, at least one of which preferably contains a dehydrohalogenation catalyst and introducing at least stream 3 into the vessel(s) under conditions effective to produce the desired fluoroolefin.

In preferred embodiments, the conversion step 51 produces a reaction product which includes not only the desired fluoroolefin, but also HF. In such embodiments it is generally preferred to introduce the stream 4 into a separation step 52 in which at least a portion of the HF is separated from the stream to produce at least a first stream 6 relatively rich (in comparison to the feed stream 4) in the fluorinated olefin and at least a second stream relatively rich (in comparison to the feed stream 4) in HF.

Preferred aspects of each of the steps 50, 51 and 52 are described below.

The Reduction Step

Although it is contemplated that the reduction step may be conducted in batch operation, it is preferred that the reduction reaction is carried out as a substantially continuous operation. Furthermore, while it is possible that the reduction reaction may involve in certain embodiments a liquid phase reaction, it is contemplated that in preferred embodiments the reduction reaction comprises, and even more preferably consists of, at least two vapor phase reaction stages.

With respect to the number of reaction stages, applicants have found surprisingly and unexpectedly found that overall reaction conversion and selectivity can be achieved at relatively high levels by the use of at least two reaction stages wherein the first stage of reaction is conducted under conditions effective to achieve a first, relatively low rate of conversion to produce a first stage reaction effluent, and at least a second stage of reaction which is fed by at least a portion of said first stage effluent and which is conducted under conditions effective to achieve a second rate of conversion higher than said first rate. Preferably, reaction conditions are controlled in each of the first and second stages in order to achieve the desired conversion in accordance with the present invention. As used herein, the term "reaction conditions" is intended to include the singular and means control of any one or more processing parameters which can be modified by the operator of the reaction to produce the conversion of the feed material in accordance with the teachings contained herein. By way of example, but not by way of limitation, conversion of the feed material may be controlled or regulated by controlling or regulating any one or more of the following: the temperature of the reaction, the flow rate of the reactants, the presence of diluent, the amount of catalyst present in the reaction vessel, the shape and size of the reaction vessel, the pressure of the reaction, and any one combinations of these and other process parameters which will be available and known to those skilled in the art in view of the disclosure contained herein.

Applicants have found that in preferred embodiments the step of controlling the conversion in the first stage of the hydrogenation reaction is achieved by judicious selection and control of the amount of catalyst present in the first stage of reaction relative to the feed rate of one or more of the reactants and/or by judicious selection and control of the reaction temperature, and preferably by judicious selection and control of both of these process parameters. The step of judiciously selecting the amount of catalyst to be used in the first stage of reaction includes the step of estimating the amount of catalyst theoretically needed to convert 100% of the feed material. Such an estimate can be obtained by any and all known methods for making such an estimate, which should be apparent to those skilled in the art in view of the teachings contained herein. In addition, the step of judiciously selecting the amount of catalyst may also involve conducting bench, pilot or similar studies to determine the amount of the particular catalyst being used which is needed to convert 100% of the feed material under the feed rate in other process parameters which have otherwise been chosen. Based upon this estimate, the preferred embodiments of the present invention then include the step of providing in the first stage of reaction an amount of catalyst that is substantially below the amount required for 100% conversion, and even more preferably is sufficiently low so as to result in a conversion of the feed olefin of from about 10% to about 60%, more preferably from about 10% to about 40%, and even more preferably from about 10% to 25%. Once again, those skilled in the art will appreciate that the step of judiciously choosing the amount of catalyst may further include running additional bench, pilot or other studies with the reduced amount of catalyst and adjusting the amount of catalyst accordingly. It is contemplated that all such studies and estimates can be achieved without undue experimentation in view of the teachings contained herein.

In preferred embodiments, therefore, the step of controlling conversion in the first reactor stage comprises feeding the olefin reactant into the first stage of reaction at a rate that is substantially above, and at least 60% about 90% above the productivity of the catalyst present in the first stage of reaction. Applicants have found, without being bound by or to any particular theory, that the use of such an excess of reactant in the first stage of reaction allows the feed materials to serve as a heat removal medium. Since the reduction or hydrogenation reaction of the present invention is generally exothermic, and usually substantially exothermic, the use of such excess feed material has the effect in preferred embodiments of maintaining the reactor temperature below that which would exist if an excess of feed material were not used, assuming all other process conditions were maintained the same.

Applicants have found that the step of maintaining a very low conversion of reactant in accordance with the present invention in a first stage of reaction has an advantageous affect on the selectivity of the reaction to the desired alkane. In other words, although the amount of conversion which occurs in the first stage of reaction is controlled to be well below that which is desired for the overall reduction step, applicants have found that an improved, higher percentage of the feed material is converted to the desired alkane in the first reaction stage (that is, improved selectivity is achieved) by controlling the conversion as described herein. More specifically, is preferred in many embodiments that the selectivity to the desired alkane in the first reaction stage is at least about 80%, more preferably at least about 90%, and even more preferably at least about 95%, and in many preferred embodiments about 97% or greater.

In certain preferred embodiments the step of controlling the conversion in the first reaction stage further includes removing heat from the reaction by cooling at least a portion of the reaction mixture. It is contemplated that those skilled in the art will be able to devise without undue experimentation and many means and mechanisms for attaining such cooling in view of the teachings contained herein and all such means and mechanisms are with the scope of the present invention.

In preferred embodiments, at least a portion of the effluent from the first reaction stage is fed directly, or optionally after some further processing, to a second reaction stage in which the unreacted fluorinated olefin remaining in the effluent after the first reaction stage is converted to the fluorinated alkane in accordance with the present invention. More specifically is preferred that the second reaction stage or subsequent reaction stages if present, is operated under conditions effective to convert the fluorinated olefin contained in the feed stream to the second reactor stage at a conversion rate that is greater than, and preferably substantially greater than, the conversion percentage in the first reaction stage. In certain preferred embodiments, for example, the conversion percentage in the second reaction stage is from about 20% to about 99%, depending in large part upon the total number of reactant stages used to affect the overall conversion step. For example, in embodiments consisting of a two-stage reaction system, it is contemplated that the conversion in the second reaction stage is preferably greater than 95%, and even more preferably about 100%. However, as those skilled in the art will appreciate from the teachings contained herein, such a two-stage reaction may not be sufficient to produce the desired selectivity to the fluorinated alkane. In such cases, it is within the scope of the present invention that the conversion step may comprise greater than two reaction stages, including in some embodiments as many 10 or more reaction stages.

In preferred embodiments, the fluorinated olefin conversion step of the present invention comprises about four reaction stages. Although it is understood that the particular parameters used in each reaction stage may vary widely within the scope of the present invention, depending upon many factors, including the desired fluorinated olefin to be produced, the available feedstock, and other specific processing constraints, the following Table provides preferred and more preferred ranges of certain process parameters applicable to certain preferred embodiments of the present invention (all numerical values in the table are understood to be preceded by the word "about.")

TABLE 1

|  |  | STAGE 1 | STAGE 2 | STAGE 3 | STAGE 4*** |
|---|---|---|---|---|---|
| REACTION TEMP, C.* | Preferred | 50-100 | 80-120 | 150-200 | 80-120 |
|  | More Preferred | 60-100 | 90-110 | 160-190 | 100-110 |
| CATALYST WEIGHT, %** | Preferred | 1-15 | 5-20 | 15-40 | 40-80 |
|  | More Preferred | 1-5 | 5-15 | 25-35 | 50-70 |
| CONVERSION, WT % | Preferred | 1-85 | 1-85 | 30-99 | 30-99 |
|  | More Preferred | 1-70 | 1-70 | 60-99 | 60-99 |
| SELECTIVITY, WT % | Preferred | 95-99 | 95-99 | 95-99 | 95-99 |
|  | More Preferred | 97-99 | 97-99 | 97-99 | 97-99 |

Figure 2:
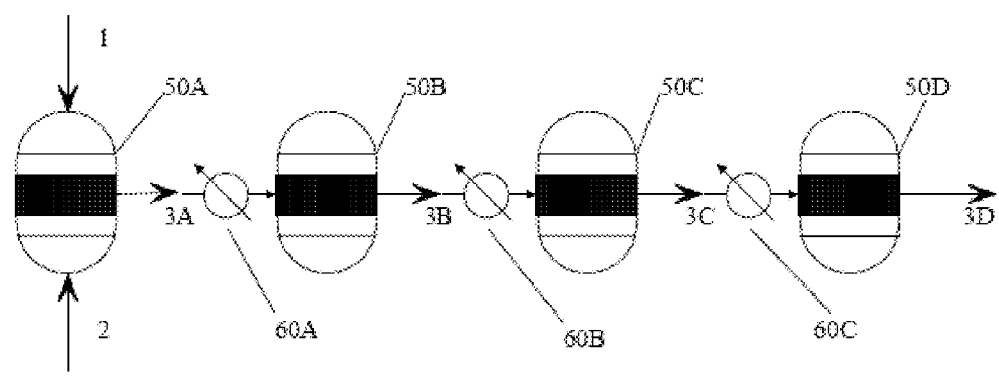
FIG. 2 is a semi-schematic process flow diagram according to one embodiment of the hydrogenation step of the present invention.

*As measured by the temperature of the reaction product effluent
**As a weight percentage of total catalyst in all stages
***Optional For the purposes of illustration but not necessarily by way of limitation, one arrangement of multiple reaction stages in accordance with a preferred reduction step in accordance with the present invention is illustrated in FIG. 2. Although it is contemplated that the reduction step 50 may be conducted in a batch-wise or semi-continuous operation, it is preferred that the reduction step 50 is a continuous operation of the general type shown in FIG. 2. In FIG. 2, a first stage reactor 50A is provided with catalyst in an amount effective to provide a conversion of the fluorinated olefin contained in stream 1 of from about 10% to about 60% in accordance with the present invention. It preferred embodiments, the first reaction stage of the present invention, for example vessel 50A, is provided with a means for cooling the reaction mixture (not shown). For example, the reaction vessel 50A may be a jacketed reaction vessel in which the space between the vessel and the jacket contains a cooling medium to remove heat from the reactor. Of course, other means for cooling the reaction mixture may be employed, such as the use of an internal cooling coil, the introduction of additional cooling diluent to the reaction mixture, and the like.

The effluent 3A from the first reaction stage is preferably, but not necessarily, further cooled prior to its introduction into the second reaction stage, such as reaction vessel 50B, for example by use of a heat exchanger 60A. In fact, in certain embodiments, it may be desirable for the heat exchanger 60A, and/or one or more of the downstream heat exchangers 60B and 60C, to provide the capability of adding heat to the effluent prior to its introduction into the next reaction stage. This capability is desirable in certain embodiments because it is generally, although not exclusively, preferred that the level of conversion in each subsequent reaction stage is higher than in the immediately preceding prior stage. In order to achieve this result, it may be desirable and/or necessary to raise the temperature of one or more of the feed streams as a means for contributing to a higher reaction temperature in the next stage of reaction. Of course, those skilled in the art will appreciate that many means and mechanisms are available for controlling the temperature in all subsequent reaction stages, and all such means and mechanisms are within the scope of the present invention and may be used to control the conversion of the reaction stage in accordance with the present invention.

The size and shape, and other characteristics of the reaction vessel itself may vary widely with the scope of the present invention, and it is contemplated that the vessel associated with each stage may be different than or the same as the vessel associated with the upstream and downstream reaction stages. Furthermore, it is contemplated that all reaction stages can occur inside a single vessel, provided that means and mechanisms necessary to control conversion are provided. For example, it may be desirable in certain embodiments to utilize a single tubular reactor for each reaction stage, providing conversion control by judicious selection of the amount and/or distribution of catalyst throughout the tubular reactor. In such a case, it is possible to further control the conversion in different sections of the same tubular reactor by controlling the amount of heat removed from or added to different sections of the tubular reactor.

Those skilled in the art will be readily able to select the type of catalyst(s) used for the hydrogenation step of the present invention in view of the teachings contained herein. For example, it is preferred in certain embodiments that at least one, but preferably all, reaction stages utilize palladium catalyst, either alone or in combination with other catalysts. In this regard one or more of the hydrogenation catalyst disclosed in U.S. Pat. No. 5,679,875, which is incorporated herein by reference, maybe used for one or more of the reaction stages in accordance with the present invention. In certain preferred embodiments, the catalyst preferably comprises palladium supported on carbon, such as a carbon mesh.

Thus, certain embodiments of the present methods comprise bringing a fluorinated olefin in accordance with formula I and a hydrogenation agent, such as $H_2$, into contact with a first amount of catalyst in a first reaction stage to produce a reaction stream comprising hydrofluorocarbon(s), unreacted fluorinated olefin and hydrogen; contacting at least a portion of this first effluent stream with a second amount of catalyst in a second stage of reaction to produce a hydrofluorocarbon, wherein the second amount of catalyst is greater than the first amount of catalyst and wherein conversion to the fluorinated olefin is higher in the second stage of reaction Preferably, at least a portion of the effluent from the second and/or any subsequent stages of reaction is then contacted with a catalyst for dehydrofluorination to produce a product stream comprising the desired fluorinated propene and HF. In certain preferred embodiments the dehydrofluorination step is followed by a preferred separation step comprising feeding at least a portion of the product stream through an extraction operation using an extraction agent, such as a stream of sulfuric acid, to extract HF from the product stream. The dehydrohalogenation step and the separation step in accordance with preferred aspects of the present invention are discussed in detail below.

Dehydrohalogenation

It is contemplated that the dehydrohalogenation reaction step may be preformed using a wide variety of process parameters and process conditions in view of the overall teachings contained herein, such as for example it is contemplated that the dehydrohalogenation step may comprise, in certain non-preferred embodiments, a liquid phase reaction. However, it is preferred in many embodiments of the present invention that this reaction step comprise a gas phase reaction, preferably in the presence of catalyst, preferably a metal catalyst, and even more preferably one or more transition metal-based catalysts (including in certain preferred embodiments transition metal halide catalysts), such as $FeCl_3$, chromiumoxyfluoride, Ni (including Ni mesh), NiCl$_2$, CrF$_3$, and mixtures thereof, supported or in bulk. Other catalysts include carbon-supported catalysts, antimony-based catalysts (such as SbCl$_5$), aluminum-based catalyst (such as AlF$_3$, Al$_2$O$_3$, and fluorinated Al$_2$O$_3$). It is expected that many other catalysts may be used depending on the requirements of particular embodiments, including for example palladium-based catalyst, platinum-based catalysts, rhodium-based catalysts and ruthenium-based catalysts. Of course, two or more any of these catalysts, or other catalysts not named here, may be used in combination.

In general it is preferred that the catalysts are fluorinated. In preferred embodiments, fluorination of the catalysts comprises exposing the catalyst to a stream of HF at about reaction temperature and pressure. The gas phase dehydrohalogenation reaction may be conducted, for example, by introducing a gaseous form of a compound of formula (II) into a suitable reaction vessel or reactor. Preferably the vessel is comprised of materials which are resistant to corrosion as Hastelloy, Inconel, Monel and/or fluoropolymers linings. Preferably the vessel contains catalyst, for example a fixed or fluid catalyst bed, packed with a suitable dehydrohalogenation catalyst, with suitable means to heat the reaction mixture to the desired reaction temperature.

While it is contemplated that a wide variety of reaction temperatures may be used, depending on relevant factors such as the catalyst being used and the most desired reaction product, it is generally preferred that the reaction temperature for the dehydrohalogentation step is from about 150° C. to about 600° C., preferably about from 200° C. to about 550° C., and even more preferably from about 220° C. to about 450° C.

In general it is also contemplated that a wide variety of reaction pressures may be used, depending again on relevant factors such as the specific catalyst being used and the most desired reaction product. The reaction pressure can be, for example, superatmospheric, atmospheric or under vacuum.

In certain embodiments, an inert diluent gas and/or an oxidizing agent, such as nitrogen, oxygen and mixture of nitrogen and oxygen, may be used in combination with the compound of formula (II) as a feed to the deydrohalogenation step. When such a diluent and/or oxidizing agent is used, it is generally preferred that the feed streamed comprise formula (II) compound in an amount of from about 5% to greater than 95% by weight based on the combined weight of diluent and formula (II) compound.

It is contemplated that the amount of catalyst used will vary depending on the particular parameters present in each embodiment. In preferred embodiments, the contact time, which is expressed as the ratio of the volume of the catalyst (ml) to the total feed flow (ml/sec) is from about 0.1 seconds to about 1000 seconds, and preferably from about 2 seconds to about 120 seconds.

One preferred dehydrohalogenation reaction comprises a dehydrofluorination reaction. For example, for embodiments in which the desired product of formula (III) is HFO-1234yf, it is preferred in certain embodiments that the compound of formula (II) comprises 1,1,1,2,3 pentafluoropropane. Applicants have found that in such embodiments it is preferred to use as the catalyst a fluorinated chromium oxide catalyst, and aluminum fluoride catalyst, a ferric fluoride catalyst, and a mixture of catalysts comprising magnesium fluoride and aluminum fluoride. In certain embodiments, nickel-based catalyst, a carbon based catalyst, or a combination of these may be used.

In addition, it is generally preferred to conduct at least a substantial portion of the reaction at a temperature of from about 200° C. to about 600° C., the particular temperature being chosen depending upon many factors, including particularly the type of catalyst being used. For example, it is preferred that when the dehydrofluorination reaction takes place in the presence of a fluorinated or fluoridated metal catalyst, then the reaction temperatures are preferably from about 200° C. to about 550° C., more preferably from about 220° C. to about 450° C., and even more preferably from about 250° C. to about 375° C. For embodiments in which the catalyst comprises activated carbon, metals on activated carbon, especially iron cobalt and nickel salts on activated carbon, and palladium on carbon, the reaction temperature is preferably from about 200° C. to about 600° C., and even more preferably from about 300° C. to about 500° C.

In preferred embodiments, the contact time is from about 0.1 sec to about 1000 seconds, and preferably from about 2 sec to about 120 seconds.

Preferably in such dehydrofluorination embodiments, the conversion is at least about 50%, more preferably at least about 65%, and even more preferably at least about 90%. Preferably, the selectivity to HFO-1234yf is at least about 70%, more preferably at least about 80% and more preferably at least about 90%.

Another preferred dehydrohalogenation reaction comprises a dehydrochlorination reaction. For example, for embodiments in which the desired product of formula (III) is HFO-1234ze, it is preferred that the compound of formula (II) comprises 1,1,1,3-tetrafluoro-3-chloropropane. Applicants have found that in certain embodiments it is preferred to use for this reaction a nickel-based catalyst at a reaction temperature of from about 200° C. to about 550° C., more preferably from about 250° C. to about 500° C., and even more preferably from about 300 to about 400° C. In certain other embodiments it is preferred to use for this reaction an activated carbon catalyst at a reaction temperature of from about 250° C. to about 550° C., more preferably from about 300° C. to about 550° C., and even more preferably about 400° C. In other embodiments it is preferred to use for this reaction a catalyst comprising 3% palladium on carbon at a reaction temperature of from about 200° C. to about 500° C., more preferably from about 225° C. to about 475° C., and even more preferably about 400° C. In yet other embodiments it is preferred to use for this reaction a catalyst comprising 2% nickel on carbon at a reaction temperature of from about 400° C. to about 500° C., more preferably from about 400° C. to about 500° C., and even more preferably about 450° C. In other embodiments it is preferred to use for this reaction a catalyst comprising chromiumoxyfluoride at a reaction temperature of from about 200° C. to about 500° C., more preferably from about 250° C. to about 450° C., and even more preferably about 300° C.

In such dehydrochlorination embodiments it is an option to introduce to the reactor inert gas and/or an oxidizing gas, such as nitrogen and/or oxygen or mixture of nitrogen and oxygen, in a formula (II):inert (or oxygen) volume ratio of from about 100:0.5 to about 100:75, with a ratio of about 100:2 being even more preferred.

In preferred aspects of the dehydrochlorination embodiments, the contact time is from about 0.1 to about 1000 sec, and preferably from about 3 to about 120 sec.

Preferably in such dehydrochlorination embodiments, the conversion is at least about 50%, more preferably at least about 65%, and even more preferably at least about 90%. Preferably, the selectivity to HFO-1234ze, and even more preferably to trans-HFO-1234ze, is at least about 70%, more preferably at least about 80% and more preferably at least about 90%.

In general the direction of flow of the gaseous components in the dehydrohalogenation step is not critical, but in certain preferred embodiments the process flow is in the down direction through a bed of the catalyst.

Preferably before each cycle of use, the dehydrohalogenation catalyst is dried, pre-treated and activated. It may also be advantageous in certain embodiments to periodically regenerate the catalyst after prolonged use while in place in the reactor. Pre-treatment may include heating the catalyst to about 250° C. to about 430° C. with a stream of nitrogen or other inert gas. The catalyst may then be activated by treating it with a stream of HF diluted with a large excess of nitrogen gas in order to obtain high catalyst activity. Regeneration of the catalyst may be accomplished by any means known in the art such as, for example, by passing air or oxygen over the catalyst at temperatures of from about 100° C. to about 400° C. for from about 1 hour to about 3 days depending on the size of the reactor.

Separation

As mentioned above, in addition to producing a fluorinated olefine, preferably fluorinated propene, the dehydrofluorination reaction also produces HF. In one preferred embodiment, HF is removed from the dehydrofluorination product stream by countercurrent extraction with sulfuric acid. In this embodiment, the product stream containing the HF is fed in one direction to a column, preferably a packed column. At the same time, a stream of sulfuric acid is fed, preferably countercurrently, to the same packed column. Appropriate column packing is readily determinable by one skilled in the art. Suitable column packing materials include those made of non-metallic polymeric materials, metals and alloys that are not reactive in the presence of HF or sulfuric acid, such as PTFE, PFA, hastelloy, monel, and noble metals. Preferably, the stream of sulfuric acid contains from about 50% to about 100% sulfuric acid, and more preferably about 80% sulfuric acid. In one embodiment, the stream of sulfuric acid is continuously fed to the top of the packed column at a feed rate of about twice the feed rate of the product stream, which in preferred embodiments is fed from the bottom of the packed column and moves in an generally upward direction substantially counter currently to the substantially down flowing stream containing the sulfuric acid. In certain embodiments, a stream comprising sulfuric acid and HF is removed from the bottom of the column and preferably at least a portion of the stream, and most preferably substantially all of the stream, is recycled back to the extraction tower. The recycling step is repeated preferably until the HF concentration in the column bottom is greater than about 10% by weight HF.

In one embodiment, the sulfuric acid and HF mixture containing greater than about 10% by weight HF is charged into a separate vessel. The mixture is then heated to a temperature sufficient to vaporize and flash off HF, which is collected. Another embodiment includes purifying the HF collected from the flash distillation.

Optionally, the HF or HCl generated from the dehydrohalogenation reaction is scrubbed from the product stream using water or caustic solutions.

The following examples are given as specific illustrations of the invention. It should be noted, however, that the invention is not limited to the specific details set forth in the examples.

EXAMPLES

Comparative Example C-1

Reaction of Hexafluoropropene and Hydrogen

A small jacketed, single stage reactor with an outer jacket connected to a circulating cooling bath of 31° C. is charged with 0.2 g of 1% Pd/C (4-6 mesh) mixed with nichrome mesh of a similar size to give a total catalyst bed volume of 1 cc. Prior to the introduction of hydrogen and hexafluoropropene gases, the bed temperature is initially about 21° C. However, when hydrogen (0.37 mol/h) and hexafluoropropene (0.26 mol/h) are introduced, the bed temperature rises to nearly 70° C. in about 1 minute.

Comparative Example C-2

Reaction of Hexafluoropropene and Hydrogen

The same small, jacketed single stage reactor as in Example C-1 is charged with a small amount of 1% Pd on carbon. Hydrogen and hexafluoropropene are premixed and then introduced into the reactor. The temperature of the catalyst bed is allowed to stabilize at 69° C. Exit gases are analyzed to determine conversion and selectivity for $CF_3CHFCF_2H$. The average conversion is 93.2% while the average selectivity is 95.7%.

Comparative Example C-3

Reaction of Hexafluoropropene and Hydrogen

Comparative Example C-2 is repeated using the same single stage reactor, except the temperature of the circulating fluid is reduced to 21° C. The temperature of the bed stabilizes at 61.5° C. Under these conditions, the conversion is reduced to 88.6% while the selectivity increases to 97.0%.

Examples 1 and 2

Multi-Stage Reduction Reactions

The reactors used in the following examples are multi-stage reactors constructed from sections of 1.5" schedule 40, 316 SS pipe.

The amount of catalyst used to charge each reaction stage is calculated by first estimating the productivity of the catalyst (grams of feed converted per gram of catalyst per hour). The productivity is estimated from scoping studies using a small reactor. Next, the desired production rate is set at about 10 lb per hour, allowing the total amount of catalyst needed for 100% conversion to be estimated. Using this information, an estimated amount of catalyst needed to convert 10-15% of the olefin in the first reactor is calculated.

Catalyst loading in the following examples is as follows:

Section 1 (1.5"×1 foot): 10g of catalyst (1 wt % Pd on 4-8 mesh carbon) with the remainder filled with ¼" SS protruded packing, catalyst equally distributed throughout.

Section 2 (1.5"×2 foot): 25 g catalyst distributed as in Section 1.

Section 3 (1.5"×3 foot): 73.4 g catalyst with 1200 cc of packing distributed as in Section 1.

Section 4 (1.5"×4 foot): 158 g of catalyst distributed with 1400 cc of packing. Total catalyst=267 g.

Example 1

Multi-Stage Reduction of Hexafluoropropene

Hexafluoropropene is introduced to the multi-stage reactor and reduced continuously over a period of 58 hours during which the average feed rate is 14.5 lb/h (or about 16.4 L per minute). The average hydrogen feed rate is 25 L per minute. Samples are taken at various points along the series of reactors to follow the percent conversion and selectivity. After the second reaction stage, the conversion is about 40%; after the fourth reaction stage, the conversion is 99.5% with selectivity for $CF_3CHFCF_2H$ of 99%. The temperature of the gases immediately exiting the reaction stages is 66° C. for the first stage, 104° C. for the second stage, 173° C. for the third stage, and 100° C. for the fourth stage. The maximum temperature in any reaction stage is about 230° C. The first bath is maintained at 55° C. while the second bath is maintained at 111° C.

Example 2

Multi-Stage Reduction of 1,2,3,3,3-Pentafluoropropene-1

1,2,3,3,3-Pentafluoropropene-1 is hydrogenated using the same reactor as in Example 1 using a feed rate of 14.6 lb/h for a total of 64 hours. The average hydrogen feed rate is 25 liters per minute. Samples are taken at various points along the series of reactors to follow the percent conversion and selectivity. After the second reactor, the conversion is about 54%. While after the fourth reactor, the conversion is 100% with the selectivity for $CF_3CHFCH_2F$ of 98%. The temperature of the gases immediately exiting the reactors is 99° C. for the first reactor, 95° C. for the second reactor, 173° C. for the third reactor, and 104° C. for the fourth reactor. The maximum temperature in any reactor is about 240° C. The first bath is maintained at 59° C., and the second bath is maintained at 116° C.

Examples 3-8

The following dehydrofluorination reactions are performed in a cylindrical Monel reactor. Heating is provided by inserting the reactor into an electric furnace. Process temperatures are recorded using a multi-point thermocouple placed inside the reactor and within the catalyst bed. The hydrofluorocarbon is fed into the bottom of the vertically mounted reactor and vaporized before reaching the catalyst bed. Effluent gases are passed through a gas sampling valve to monitor the progress of the reaction using GC analysis.

Example 3

Dehydrofluorination of 1,1,1,2,3,3-hexafluoropropane (HFC-236ea) over Fluorinated $Cr_2O_3$ Catalyst HFC-236ea is passed over 20 cc of fluorinated $Cr_2O_3$ at a rate of 12 g/h at a temperature range of from 250 to 350° C. at 1 atm. Two isomers of 1,1,1,2,3-pentafluoropropene, specifically, 1225yeZ and 1225yeE, are generated during the reaction. As shown in Table Ex3 below, as the reaction temperature increases from 250 to 350° C., the conversion of HFC-236ea is increased from 65.2% to 96.0%, while the selectivity to 1225yeZ is slightly decreased from 97.0% to 94.6%. At 250° C., 1225 isomers appear to be the only products. These results indicate that the fluorinated $Cr_2O_3$ catalyst is very active and selective for converting HFC-236ea to 1225yeZ.

TABLE Ex3

Effect of reaction temperature on the performance of fluorinated Cr2O3 during dehydrofluorination of HFC-236ea

| Temp (° C.) | 236ea conversion (%) | 1225yeZ selectivity (%) | 1225yeE selectivity (%) | Unknown selectivity (%) |
|---|---|---|---|---|
| 350 | 96.0 | 94.6 | 4.0 | 1.4 |
| 300 | 90.2 | 96.3 | 3.5 | 0.2 |
| 275 | 81.5 | 96.9 | 3.0 | 0.1 |
| 250 | 65.2 | 97.0 | 3.0 | 0.0 |

Example 4

Dehydrofluorination of HFC-236ea over Metal Fluoride Catalysts

The catalysts for use in this example include $AlF_3$, $FeF_3$, and 10% $MgF_2$-90% $AlF_3$. HFC-236ea is passed over 20 cc of each catalyst at a rate of 12 g/h at 350° C. at 1 atm. As shown in Table Ex4 below, both $AlF_3$ and 10% $MgF_2$-90% $AlF_3$ provide high activity (>95% HFC-236ea conversion) for dehydrofluorination of HFC-236ea, while $FeF_3$ exhibits much lower activity (<60% HFC-236ea conversion). The selectivity to 1225yeZ over the $AlF_3$ and 10% $MgF_2$-90% $AlF_3$ catalysts is about 92% at 350° C.

TABLE Ex4

Dehydrofluorination of HFC-236ea over metal fluoride catalysts

| Catalyst | 236ea conversion (%) | 1225yeZ selectivity (%) | 1225yeE selectivity (%) | Unknown selectivity (%) |
|---|---|---|---|---|
| $AlF_3$ | 96.8 | 92.8 | 3.9 | 3.3 |
| $FeF_3$ | 55.4 | 96.4 | 3.0 | 0.6 |
| 10% $MgF_2$—90% $AlF_3$ | 98.3 | 92.0 | 4.0 | 4.0 |

Example 5

Dehydrofluorination of HFC-236ea over Activated Carbon Supported Metal Catalysts The catalysts for use in this example include three activated carbon supported metal catalysts, specifically, 0.5 wt % Fe/AC, 0.5 wt % Ni/AC, and 5.0 wt % Co/AC. HFC-236ea is passed over 20 cc of each catalyst at a rate of 12 g/h at 350° C. at 1 atm. As shown in Table Ex5, among the activated carbon supported non-precious metal catalysts, iron exhibits the highest activity. At a reaction temperature of 350° C. and 1 atm, the 0.5 wt % Fe/AC catalyst provides a 1225yeZ selectivity of about 90% and an HFC-236ea conversion of about 80%.

TABLE Ex5

Dehydrofluorination of HFC-236ea over activated carbon supported metal catalysts at 350 °C.

| Catalyst | 236ea conversion (%) | 1225yeZ selectivity (%) | 1225yeE selectivity (%) | Unknown selectivity (%) |
|---|---|---|---|---|
| 0.5 wt % Fe/AC | 80.0 | 88.5 | 2.7 | 8.8 |
| 0.5 wt % Ni/AC | 24.8 | 61.3 | 1.9 | 36.8 |
| 5.0 wt % Co/AC | 10.9 | 26.5 | 0.8 | 72.7 |

Example 6

Dehydrofluorination of $CF_3CHFCH_2F$ (HFC-245eb) over Fluorinated Alumina and Chromium Oxide Catalysts The catalysts for use in this example include two fluorinated metal oxide catalysts, specifically, fluorinated $Al_2O_3$ and $Cr_2O_3$. HFC-245eb is passed over 20 cc of each catalyst at a rate of 12 g/h at 300° C. at 1 atm. 2,3,3,3-Tetrafluoropropene (HFC-1234yf) is generated as a reaction product. As shown in Table Ex6, both fluorinated metal oxide catalysts provide an HFC-245eb conversion above 95% and 1234yf selectivity above 96%. These results indicate that the fluorinated $Al_2O_3$ and $Cr_2O_3$ catalysts are very active and selective for converting 245eb into 1234yf.

TABLE Ex6

Dehydrofluorination of HFC-245eb over fluorinated metal oxide catalysts

| Catalyst | 245eb conversion (%) | 1234yf selectivity (%) | Unknown selectivity (%) |
|---|---|---|---|
| fluorinated $Al_2O_3$ | 95.2 | 96.9 | 3.1 |
| fluorinated $Cr_2O_3$ | 97.5 | 96.5 | 3.5 |

Example 7

Dehydrofluorination of HFC-245eb over Metal Fluoride Catalysts

The catalysts for use in this example include three metal fluoride catalysts, specifically, $MgF_2$, $AlF_3$, and $CeF_4$. HFC-245eb is passed over 20 cc of each catalyst at a rate of 12 g/h at 350° C. at 1 atm. As shown in Table Ex7, among the metal fluorides investigated, $AlF_3$ exhibits the highest activity with high selectivity. This catalyst provides an HFC-245eb conversion of about 97% and a 1234yf selectivity of about 97%.

TABLE Ex7

Dehydrofluorination of HFC-245eb over metal fluoride catalysts

| Catalyst | 245eb conversion (%) | 1234yf selectivity (%) | Unknown selectivity (%) |
|---|---|---|---|
| $MgF_2$ | 45.5 | 99.2 | 0.8 |
| $AlF_3$ | 96.8 | 96.7 | 3.3 |
| $CeF_4$ | 73.4 | 98.4 | 1.6 |

Example 8

Dehydrofluorination of HFC-245eb over Activated Carbon and Activated Carbon-Supported Pd Catalysts The catalysts for use in this example include activated carbon and activated carbon-supported Pd catalysts. HFC-245eb is passed over 20 cc of each catalyst at a rate of 12 g/h at 1 atm. As shown in Table Ex8, the activated carbon shows very low activity for converting 245eb into 1234yf even at 525° C., while the 0.5 wt % activated carbon-supported Pd catalyst provides a 245eb conversion of about 92% and a 1234yf selectivity of about 98% at 450° C. These results indicate zero-valent metal catalysts can be active for the dehydrofluorination of 245eb to 1234yf.

TABLE Ex8

Dehydrofluorination of HFC-245eb over activated carbon (AC) and AC supported Pd catalysts

| Catalyst | Temperature (° C.) | 245eb conversion (%) | 1234yf selectivity (%) | Unknown selectivity (%) |
|---|---|---|---|---|
| AC | 525 | 5.4 | 97.4 | 2.6 |
| 0.5 wt % Pd/AC | 450 | 92.6 | 98.6 | 1.4 |

Example 9

Sulfuric Acid Extraction of HF Generated from Dehydrofluorination Reaction

The product stream of Example 3 (at 350° C.), which contains 4.0 wt % HFC-236ea, 78.9 wt % 1225yeZ, 3.3 wt % 1225yeE, 12.6 wt % HF, and 1.2% unknown is fed to the bottom of a packed column at a feed rate of about 2.9 lbs per hour for about 4 hours.

A stream of about 80 wt % sulfuric acid (80/20$H_2SO_4$/$H_2O$) is fed continuously to the top of the same packed column at a feed rate of about 5.6 lbs per hour during the same time frame. A gaseous stream exiting the top of the column includes a majority of the organics with less than 0.5 wt % HF. The concentration of HF in the sulfuric acid in the column bottoms is about 5.8 wt %.

The column bottoms containing sulfuric acid and HF are recycled back to the extraction tower until the HF concentration is greater than 10 wt % HF. Subsequently, the sulfuric acid and HF mixture is charged into a 2 gallon Teflon® vessel. The mixture is heated to about 140° C. to vaporize and flash off HF, which is collected. The collected HF product contains 6000 ppm water and 217 ppm sulfur. The sulfuric acid contains about 500 ppm of total organic carbon.

The HF collected from flash distillation is distilled in a distillation column, and anhydrous HF is recovered. The recovered anhydrous HF contains about 37 ppm of sulfur impurities.

Example 10

Conversion of 1-bromo, 2,3,3,3-tetrafluoropropene to 2,3,3,3-tetrafluoropropene 1-bromo, 2,3,3,3-tetrafluoropropene is introduced to the multi-stage reactor of Example 1 and reduced continuously. Samples are taken at various points along the series of reactors to follow the percent conversion and selectivity. After the second reaction stage, the conversion is about 40%; after the fourth reaction stage, the conversion is 99.5% with selectivity for $CF_3CHFCH_2Br$ of 99%.

The alkane product produced in the multistage reactor are introduced into a catalytic reactor where it is dehydrochlorinated to 2,3,3,3-tetrafluoropropene at a high level of conversion and selectivity.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the spirit and script of the invention, and all such variations are intended to be included within the scope of the following claims.

What is claimed is:

1. A process for producing a fluorinated olefin having from three to six carbon atoms and a degree of halogen substitution of N, the process comprising the steps of:
   (a) converting, in at least two reaction stages, a fluorinated olefin having a degree of halogen substitution of N+1 to at least one fluorinated alkane having a degree of halogen substitution of N+1; and
   (b) converting said fluorinated alkane to a fluorinated olefin having a degree of halogen substitution of N and substantially the same number of carbon atoms as the fluorinated olefin starting material;
wherein the first of said at least two reaction stages provides a conversion of said fluorinated olefin starting material of from about 10% to about 60%, and the second of said at least two reaction stages provides a conversion of said fluorinated olefin starting material at a conversion rate that is greater than the conversion in said first stage.

2. The process of claim 1 wherein said converting step (b) produces a reaction product stream comprising HF and the fluorinated olefin having a degree of fluorine substitution of N.

3. The process of claim 2 wherein at least a portion of said reaction product stream from the converting step (b) is contacted with sulfuric acid to extract HF from said product stream.

4. The process of at least a portion of claim 3 wherein said sulfuric acid contacting step produces an effluent sulfuric acid stream containing at least a portion of the HF from the reaction product stream and wherein said process further comprises the step of recycling at least a portion of said effluent sulfuric acid stream through said extraction tower.

5. The process of claim 1 wherein said fluorinated olefin having a degree of substitution of N+1 comprises at least one fluoropropene having from three to six fluorine substituents.

6. The process of claim 5 wherein said fluorinated olefin having a degree of substitution of N+1 comprises hexafluoropropene.

7. The process of claim 5 wherein said fluorinated olefin having a degree of substitution of N+1 comprises pentafluoropropene.

8. The process of claim 5 wherein said fluorinated alkane comprises chlorotrifluoropropane (HCFC-244).

9. The process of claim 5 wherein said fluorinated alkane comprises pentafluoropropane (HFC-245).

10. The process of claim 5 wherein said fluorinated alkane comprises hexafluoropropane (HFC-236).

11. The process of claim 1 wherein said fluorinated olefin having a degree of fluorine substitution of N+1 comprises $F_2C=CFCF_3$.

12. The process of claim 1 wherein said fluorinated olefin having a degree of fluorine substitution of N+1 comprises $CFH=CFCF_3$.

13. The process of claim 1 wherein said converting step (a) comprises at least a first and second stage of catalytic hydrogenation reaction.

14. The process of claim 13 wherein said converting step (a) comprises the use of carbon-supported palladium in each of said first and second reaction stages.

15. The process of claim 1 wherein said converting step (b) comprises dehydrohalogenation.

16. The process of claim 15 wherein said dehydrohalogenation comprises catalyzed dehydrofluorination.

17. The process of claim 16 wherein said dehydrofluorination comprises a catalyzed reaction and said catalyst is selected from the group consisting of one or more fluorinated metal oxides, metal fluorides, carbon supported transition metals and combinations of these.

18. A process for the production of fluorinated olefins comprising the steps of:
   (a) hydrogenating, in a multistage reaction, a compound of formula (I)

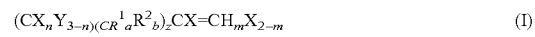

under conditions effective to form at least one fluorinated alkane of formula (II)

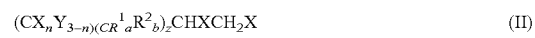

where:
   each X is independently Cl, F, I or Br;
   each Y is independently H, Cl, F, I or Br;
   each $R^1$ is independently H, Cl, F, I, Br or unsubstituted or halogen substituted methyl or ethyl radical;
   each $R^2$ is independently H, Cl, F, I, Br or unsubstituted or halogen substituted methyl or ethyl radical;
   n is 1, 2 or 3;
   a and b are each 1 or 2, provided that a+b=2;
   m is 0, 1 or 2; and (b) dehydrohalogenating the compound of formula (II) under conditions effective to produce a compound of formula (III):

$$(CX_nY_{3-n})(CR^1{}_aR^2{}_b)_zCX=CH_mX_{2-m} \qquad (III)$$

provided that each n is the same value as in formula (I), m is 0 or 1, and the compound of formula (III) has a lower degree of fluorine substitution than the compound of formula (I);

wherein a first stage of said multistage reaction provides a conversion of said compound of formula (I) of from about 10% to about 60%, and a second stage of said multistage reaction provides a conversion of said compound of formula (I) at a conversion rate that is greater than the conversion in said first stage.

* * * * *